United States Patent [19]

Weisburg et al.

[11] Patent Number: 5,552,279

[45] Date of Patent: Sep. 3, 1996

[54] NUCLEIC ACID PROBES FOR THE DETECTION OF MYCOPLASMA PNEUMONIAE AND MYCOPLASMA GENITALIUM

[75] Inventors: William G. Weisburg, Milford; Dale A. Pelletier, Brighton, both of Mass.

[73] Assignee: Amoco Corporation, Chicago, Ill.

[21] Appl. No.: 283,067

[22] Filed: Jul. 29, 1994

Related U.S. Application Data

[63] Continuation of Ser. No. 673,686, Mar. 22, 1991, abandoned.

[51] Int. Cl.$^6$ .............................. C12Q 1/68; C07H 21/00
[52] U.S. Cl. .............................................. 435/6; 536/24.32
[58] Field of Search ............................... 435/6; 536/24.32

[56] References Cited

U.S. PATENT DOCUMENTS 4,581,333  3/1986  Kourilsky et al. .................... 435/6

FOREIGN PATENT DOCUMENTS

| | | |
|---|---|---|
| 0250662 | 1/1988 | European Pat. Off. . |
| 0272009 | 6/1988 | European Pat. Off. . |
| 0305145 | 3/1989 | European Pat. Off. . |
| WO88/03957 | 6/1988 | WIPO . |

OTHER PUBLICATIONS

Dams et al., *Nuc. Acid Res.*, 16:r87–r173 (1988).
Göbel et al., *J. Gen. Microbiol.*, 133:1969–1974 (1987).
Hyman et al., *J. Clin. Microbiol.*, 25:726–728 (1987).
Peterson et al., *Nucleic Acid Res.*, 19:6029–6031 (1991).
Rogers et al., *Proc. Natl. Acad. Sci. USA*, 82:1160–1164 (1984).
Weisburg et al., *J. Bacteriology*, 171:6455 (1989).
Woese et al., *Proc. Natl. Acad. Sci. USA*, 77:494–498 (1980).
Genback Locus IDS: EOORGNB (1981), BACRGRRNB (1983), PARRN23S (1987), N80802 (1990), N80803 (1990).
EMBL Locus Record: MRCRRNAPN (1990).
GCG Word Search No. of Hits (Diagonals) on GENBANK LOCUS MYCRRNAPN.
GENBANK LOCI MYCRRNAPN, MYCRRNAPI, MYCRRNAN, MYCRRNAF, MYCRRNAI, MYCRRNAAG.
GENALIGN ALIGNMENT of MYCRRNAM, MYCRRNAPI, MYCRRNAN, MYCRRNAF, MYCRRNAI, MYCRRNAAG.
Gutell et al, A Complation of Large Subumit RNA Sequences Presented in a Structural Format Nucl. Acids Res. (1988) vol. 16 (Supplement) r175–r269.
GCG Search Printout for SEQ ID Numbers:1–20.

*Primary Examiner*—W. Gary Jones
*Assistant Examiner*—David Schreiber
*Attorney, Agent, or Firm*—Norval B. Galloway

[57] ABSTRACT

Nucleic acid probes are described for detecting the principle etiological agent of primary atypical pneumonia, *Mycoplasma pneumoniae*, or, optionally, *Mycoplasma pneumoniae* and *Mycoplasma genitalium*. Said probes are complementary to ribonucleic acid sequences found in these mycoplasmas and absent from other mycoplasma, other bacterial, animal, or plant genomes. As such, these probes can detect the rRNA, rDNA, or polymerase chain reaction amplification products from these mycoplasma species. This set of probes, plus the described amplification primers, circumscribe a method for detecting the etiological agents of atypical pneumonia, and for making a clinical diagnosis of this disease. This set of probes also circumscribes a method for identification of these infectious agents in culture media enrichments inoculated from clinical samples.

22 Claims, 1 Drawing Sheet

NUCLEIC ACID PROBES FOR THE DETECTION OF MYCOPLASMA PNEUMONIAE AND MYCOPLASMA GENITALIUM

This is a continuation of application Ser. No. 07/673,686 filed Mar. 22, 1991, now abandoned.

FIELD OF THE INVENTION

This invention relates to the detection of *Mycoplasma pneumoniae,* the causative agent of human primary atypical pneumonia. More specifically, it provides nucleic acid compositions and methods for their use for the specific detection of *Mycoplasma pneumoniae* in clinical and other samples. The nucleic acid compositions feature nucleotide sequences, from 10 to 250 nucleotides, which are capable of hybridizing preferentially to the rRNA and rDNA of *Mycoplasma pneumoniae.*

BACKGROUND OF THE INVENTION

Mycoplasmas are small wall-less bacteria, primarily isolated from animal sources including humans. There are over 70 members of the genus Mycoplasma, and several related genera which are also characterized by small wall-less bacteria; these are Spiroplasma, Acholeplasma, Ureaplasma, Anaeroplasma, and Asteroleplasma. Only a handful of the species within these genera have been found associated with humans—some presumed to be "normal flora", others suspected of being pathogenic, and only one species known to be an important cause of human morbidity, whenever it is isolated. *Mycoplasma pneumoniae* is an important cause of primary atypical pneumonia and several nonrespiratory complications. The indication of its presence always provides clinically relevant information. Other pathogenic mycoplasma organisms comprise *Mycoplasma fermentans, Mycoplasma hominis, Ureaplasma urealyticum* and *Mycoplasma genitalium.* Nucleic acid compositions and methods for the detection of these organisms are the subject of two concurrently filed applications U.S. Ser. No. 07/673,661 and U.S. Ser. No. 07/673,687, now abandoned, entitled "Nucleic Acid Probes For The Detection of Genital Mycoplasmas" and "Nucleic Acid Probes For The Detection of Mycoplasma Fermentans Or The Aids-Associated Virus-Like Infectious Agent." At least one inventor is common to both of these applications and the present application.

The mycoplasmas, such as *Mycoplasma pneumoniae,* are fastidious organisms, requiring complex culture media containing peptone, yeast extract, expensive animal sera, and a sterol. Growth is relatively slow and reaches low cell densities compared to most bacteria. In addition, cell growth requires the addition of carbon dioxide to the surrounding atmosphere. For these reasons, many clinical laboratories are unable to perform culture isolation of *M. pneumoniae,* and consequently are left with no real ability to diagnose the presence of this important pathogenic bacteria. Given that mycoplasmas lack cell walls, antibiotics that target the bacterial cell wall, such as penicillin, have no anti-mycoplasma activity. Consequently, it is of importance for a physician to make a diagnosis of atypical pneumonia and prescribe the appropriate antibiotic.

Several investigators have discussed the similarity of *Mycoplasma pneumoniae* to *Mycoplasma genitalium* both serologically (Lind, et al., J. Clinical Microbiol., vol. 20, 1984) and within DNA sequences including the rRNA operons (Yogev and Razin, Int. Jnl. System. Bacteriol., vol. 36, 1986). Weisburg, et al. discuss the various other evolutionary relatives of *M. pneumoniae* (Jnl. of Bacteriol., vol. 171, 1989).

*M. genitalium* may possibly have a role in respiratory infection either in co-culture with *M. pneumoniae* or in the absence of *M. pneumoniae* (Tully, Clinical Micro. Newsletter, vol. 11, 1989). *Mycoplasma genitalium* may be responsible for some fraction of clinical atypical pneumonia.

While Kohne et al. (Biophysical Journal 8:1104–1118, 1968) discuss one method for preparing probes to rRNA sequences, they do not provide the teaching necessary to make probes to detect *Mycoplasma pneumoniae* or *M. pneumoniae* in combination with *M. genitalium.*

Pace and Campbell (Journal of Bacteriology 107:543–547, 1971) discuss the homology of ribosomal ribonucleic acids from diverse bacterial species and a hybridization method for quantitating such homology levels. Similarly, Sogin, Sogin and Woese (Journal of Molecular Evolution 1:173–184, 1972) discuss the theoretical and practical aspects of using primary structural characterization of different ribosomal RNA molecules for evaluating phylogenetic relationships. Fox, Pechman and Woese (International Journal of Systematic Bacteriology 27:44–57, 1977) discuss the comparative cataloging of 16S ribosomal RNAs as an approach to prokaryotic systematics.

Hogan, et al. (International Patent Application, Publication Number WO 88/03957) describe five putative *M. pneumoniae* specific probes, but they were not tested in a manner which allowed evaluation of *M. genitalium* cross-reactivity by rigorous criteria. Their mixture of four probes reacted 10 times more strongly with *M. genitalium* than with the related species. *M. gallisepticum.* None of their probes target the 23S rRNA molecule. Probes disclosed appear to be unable to distinguish a known homologous sequence from *M. genitalium.*

Zivin and Monahan, European Patent application publication number 0305145A2, describe several probes which were designed based on the determination of 307 bases of the 5' end of *M. pneumoniae.* They claim anecdotally to exclude *M. genitalium* with some of their probes.

Gobel, et al. discuss probes for Mycoplasmas including *M. pneumoniae* (Gobel, et.al., Israel Jnl. of Med. Sci. vol. 23, 1987) but fail to teach what the structure of these probes is. Further, in an EP patent application number, EP0250662A1, Gobel et al. suggest probes to *M. pneumoniae;* however, such probes may lack the sensitivity or specificity for clinical applications and are not suitable for solution hybridization formats.

Rogers, et al. discuss sequences of 5S rRNA of mycoplasmas (Rogers et al., Proc. Natl. Acad. Sci. USA, vol. 82, 1985). Rogers, et al. do not suggest any sequences which would be useful to facilitate detection of these organisms and do not discuss 16S or 23S rRNA sequences. Woese, et al. discuss 16S rRNA oligonucleotide catalogs of selected mycoplasma species, but do not discuss probes or *Mycoplasma pneumoniae.*

Bernet, et al. discuss polymerase chain reaction detection of *Mycoplasma pneumoniae* (Bernet, et al., Jnl. Clin. Micro., vol. 27, 1989), but not directed toward rRNA or rDNA sequences. Hyman, et al. also discuss polymerase chain reaction detection of *Mycoplasma pneumoniae* and *Mycoplasma genitalium* (Hyman, et al., Jnl. Clin. Micro., vol. 25, 1987), but fail to discuss the utility of rRNA or rDNA sequences.

Gobel, et al. discuss mycoplasma rRNA probes in a publication, (Gobel, et al., Jnl. Genl. Micro., vol 133, 1987).

However, Gobel, et al. do not recognize the significance of discrimination of probes toward other mycoplasma species, particularly *Mycoplasma genitalium*.

Ribosomes are of profound importance to all organisms because they serve as the only known means of translating genetic information into cellular proteins, the main structural and catalytic elements of life. A clear manifestation of this importance is the observation that all cells have ribosomes.

Bacterial ribosomes contain three distinct RNA molecules which, at least in *Escherichia coli*, are referred to as 5S, 16S and 23S rRNAs. In eukaryotic organisms, there are four distinct rRNA species, generally referred to as 5S, 18S, 28S, and 5.8S. These names historically are related to the size of the RNA molecules, as determined by their sedimentation rate. In actuality, however, ribosomal RNA molecules vary substantially in size between organisms. Nonetheless, 5S, 16S, and 23S rRNA are commonly used as generic names for the homologous RNA molecules in any bacterium, including the mycoplasmas, and this convention will be continued herein.

As used herein, probe(s) refer to synthetic or biologically produced nucleic acids (DNA or RNA) which, by design or selection, contain specific nucleotide sequences that allow them to hybridize under hybridization conditions, preferentially to target nucleic acid sequences. The term "preferentially" is used in a relative sense; one hybridization reaction product is more stable than another under identical conditions.

In addition to their hybridization properties, probes also may contain certain constituents that pertain to their proper or optimal functioning under particular assay conditions. For example, probes may be modified to improve their resistance to nuclease degradation (e.g. by end capping), to carry detection ligands (e.g. fluorescein, biotin, and avidin), to facilitate direct or indirect detection ($^{32}$P, and fluorescent and chemiluminescent agents) or to facilitate their capture onto a solid support (e.g., homopolymer "tails"). Such modifications are elaborations on the basic probe function which is its ability to usefully discriminate between target and non-target organisms in a hybridization assay.

Hybridization traditionally is understood as the process by which two partially or completely complementary strands of nucleic acid are allowed to come together in an antiparallel fashion (one oriented 5' to 3', the other 3' to 5') to form a double-stranded nucleic acid with specific and stable hydrogen bonds, following explicit rules pertaining to which nucleic acid bases may pair with one another. The high specificity of probes relies on the low statistical probability of unique sequences occurring at random as dictated by the multiplicative product of their individual probabilities. Normal hybridization conditions for nucleic acid of approximately 10 to 250 nucleotides would include a temperature of approximately 60° C. in the presence of 1.08M sodium chloride, 60 mM sodium phosphate and 6 mM ethylenediamine tetraacetic acid (pH 7.4).

Hybridization conditions are easily modified to suit nucleic acids of differing sequences. Factors which may influence the hybridization conditions for a particular nucleic acid composition are base composition of the probe/target duplex, as well as by the level and geometry of mispairing between the two nucleic acids.

Reaction parameters which are commonly adjusted are the concentration and type of ionic species present in the hybridization solution, the types and concentrations of denaturing agents present, and the temperature of hybridization. Generally, as hybridization conditions become more stringent, or less favorable for hybridization, longer probes are required to form stable hybrids.

SUMMARY OF THE INVENTION

The present invention features nucleic acid compositions and composition sets and methods for the specific detection or identification of pathogenic mycoplasma bacteria associated with human primary atypical pneumonia. One embodiment of the present invention features, as a composition of matter, a nucleic acid having approximately 10 to 250 nucleotides capable of hybridizing to rRNA or rDNA of pathogenic mycoplasma bacteria associated with human primary atypical pneumonia in preference to rRNA or rDNA of nonmycoplasma bacteria and humans. The nucleic acid composition is useful for detecting *Mycoplasma pneumoniae*, and *Mycoplasma genitalium*.

Embodiments of the present invention feature nucleic acids capable of hybridizing to 16S rRNA or 16S rDNA of *Mycoplasma pneumoniae* and 23S rRNA or 23S rDNA of *Mycoplasma pneumoniae*. One embodiment of the present invention features a nucleic acid capable of hybridizing to 16S rRNA or 16S rDNA, or 23S rRNA or 23S rDNA of both *Mycoplasma pneumoniae* and *Mycoplasma genitalium*. The nucleic acid compositions are complementary to or homologous with a region of rRNA or rDNA selected from the group of regions consisting of positions 1110 to 1160 or 1220 to 1270 of the *Mycoplasma pneumoniae* 16S rRNA, positions 150 to 200, 260 to 340, 1590 to 1630, 2080 to 2190 or 2600 to 2660 of the *Mycoplasma pneumoniae* 23S rRNA, positions 50 to 100, 140 to 230, 440 to 500, 620 to 670, 810 to 860, 980 to 1030, or 1210 to 1270 of the *Mycoplasma pneumoniae* and *Mycoplasma genitalium* 16S rRNA, and positions 330 to 370 of the *Mycoplasma pneumoniae* and *Mycoplasma genitalium* 23S rRNA. All such numerical designations are nucleotide positions counted from the 5' end of the RNA molecule, a convention known to those skilled in the art. Those nucleic acid compositions of the present invention that are capable of hybridizing to rRNA or rDNA of both *Mycoplasma pneumoniae* and *Mycoplasma genitalium* have utility in two-probe systems in which one of the two probes is capable of distinguishing between the two organisms. Thus, one embodiment of the present invention comprises an article of manufacture. The article of manufacture comprises a set of nucleic acids comprising at least two nucleic acids. Each nucleic acid has 10 to 250 nucleotides and each nucleic acid has a different base sequence composition. At least one of the nucleic acids of the set is complementary to or homologous with at least 90% of a sequence comprising any ten consecutive nucleotides selected from the group of sequences defined by probes consisting of 2295 (SEQ ID NO:1), 2289 (SEQ ID NO:2), 2296 (SEQ ID NO:3), 2298 (SEQ ID NO:4), 2299 (SEQ ID NO:5), 2300 (SEQ ID NO:6), 2294 (SEQ ID NO:7), 2167 (SEQ ID NO:8), 2196 (SEQ ID NO:9), 2297 (SEQ ID NO:10), 2192 (SEQ ID NO:11), 2219 (SEQ ID NO:12), 2162 (SEQ ID NO:13), 2202 (SEQ ID NO:14), 2201 (SEQ ID NO:15), 2166 (SEQ ID NO:16), 2224 (SEQ ID NO:17), 2195 (SEQ ID NO:18), 2225 (SEQ ID NO:19), and 2230 (SEQ ID NO:20).

Preferably, at least two nucleic acid compositions are complementary or homologous with at least 90% of a sequence comprising ten consecutive nucleotides selected from the group of sequences defined by probes, and selected from the group of sets consisting of, Probe 2196 (SEQ ID NO:9) and Probe 2167 (SEQ ID NO:8); Probe 2162 (SEQ ID NO:13) and Probe 2202 (SEQ ID NO:14);

Probe 2224 (SEQ ID NO:17) and Probe 2166 (SEQ ID NO:16); Probe 2162 (SEQ ID NO:13) and Probe 2230 (SEQ ID NO:20);

Probe 2167 (SEQ ID NO:8) and Probe 2219 (SEQ ID NO:12); Probe 2192 (SEQ ID NO:11) and Probe 2202 (SEQ ID NO:14);

Probe 2296 (SEQ ID NO:3) and Probe 2297 (SEQ ID NO:10); and, Probe 2299 (SEQ ID NO:5) and Probe 2300 (SEQ ID NO:6).

A further embodiment of the present invention features a method for detecting the presence of one or more mycoplasmas which consist essentially of *Mycoplasma pneumoniae* and *Mycoplasma genitalium* in a sample. The method includes the steps of contacting a sample with at least one nucleic acid having approximately 10 to 250 nucleotides capable of hybridizing preferentially to mycoplasma rRNA and rDNA. The method includes imposing hybridization conditions on the sample which conditions allow the nucleic acid to bind preferentially to mycoplasma rRNA and rDNA to form nucleic acid complexes. The nucleic acid complexes are detected as an indication of the mycoplasma.

Preferably, the nucleic acid of the contacting step is complementary to or homologous with at least 90% of a sequence comprising any ten consecutive nucleotides selected from the group of sequences defined by probes 2295 (SEQ ID NO:1), 2289 (SEQ ID NO:2), 2296 (SEQ ID NO:3), 2298 (SEQ ID NO:4), 2299 (SEQ ID NO:5), 2300 (SEQ ID NO:6), 2294 (SEQ ID NO:7), 2167 (SEQ ID NO:8), 2196 (SEQ ID NO:9), 2297 (SEQ ID NO:10), 2192 (SEQ ID NO:11), 2219 (SEQ ID NO:12), 2162 (SEQ ID NO:13), 2202 (SEQ ID NO:14), 2201 (SEQ ID NO:15), 2166 (SEQ ID NO:16), 2224 (SEQ ID NO:17), 2195 (SEQ ID NO:18), 2225 (SEQ ID NO:19), and 2230 (SEQ ID NO:20).

One embodiment of the present invention features a contacting step utilizing two nucleic acid compositions. Each nucleic acid has 10 to 250 base sequences capable of hybridizing preferentially to mycoplasma rRNA and rDNA and each having a different base composition. The nucleic acids are complementary to or homologous with at least 90% of a sequence comprising any 10 consecutive nucleotides selected from the group of sequences defined by probes and selected from the group of sets consisting of, Probe 2196 (SEQ ID NO:9)+Probe 2167 (SEQ ID NO:8), Probe 2162 (SEQ ID NO:13)+Probe 2202 (SEQ ID NO:14)

Probe 2224 (SEQ ID NO:17)+Probe 2166 (SEQ ID NO:16), Probe 2162 (SEQ ID NO:13)+Probe 2230 (SEQ ID NO:20)

Probe 2167 (SEQ ID NO:8)+Probe 2219 (SEQ ID NO:12), Probe 2192 (SEQ ID NO:11)+Probe 2202 (SEQ ID NO:14)

Probe 2296 (SEQ ID NO:3)+Probe 2297 (SEQ ID NO:10), Probe 2299 (SEQ ID NO:5)+Probe 2300 (SEQ ID NO:6).

A further embodiment of the present invention features a kit for detecting pathogenic mycoplasma bacterium associated with human primary atypical pneumonia. The kit has a nucleic acid composition having 10 to 250 base sequences, capable of hybridizing to rRNA or rDNA of pathogenic mycoplasma bacteria in preference to rRNA and rDNA of nonmycoplasma and humans.

Typically, kits are comprised of reagents, compositions, instructions, disposable hardware and suitable packaging to allow marketing a convenient assembly.

The nucleic acid compositions, kits, and methods of the present invention provide the basis for development of valuable nucleic acid hybridization assays for the specific detection of atypical pneumonia or its etiological agent. The type of samples which may be encountered include sputum, throat swabs, blood, urine, cerebrospinal fluid, skin, biopsy, saliva, synovial fluid, bronchial wash, bronchial lavage, or other tissue or fluid samples from human patients or veterinary subjects.

The discovery that probes could be generated with the extraordinary inclusivity and exclusivity characteristics of the present invention with respect to the detection of a panel of *M. pneumoniae* and *M. genitalium* isolates, without necessarily incurring cross-reactivity between these species, was unpredictable and unexpected.

BRIEF DESCRIPTION OF THE FIGURE

Further understanding of the principles and aspects of the present invention may be made by reference to the tables and figures.

DETAILED DESCRIPTION OF THE INVENTION AND BEST MODE

Probe Development Strategy

Figure 1:
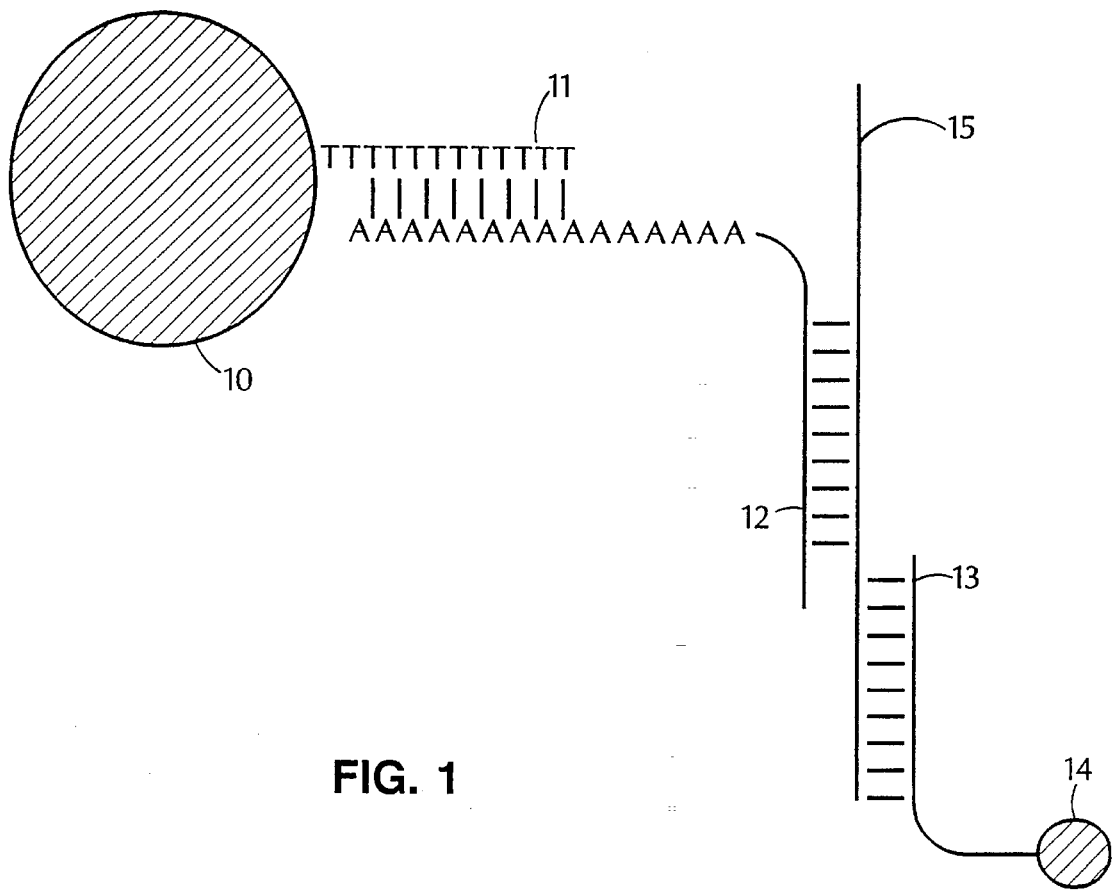
FIG. 1 is a schematic representation of a dual probe capture/detector assay.

The first step taken in the development of nucleic acid compositions of the present invention involved identification of regions of the 16S rRNA which potentially could serve as target sites for specific probes with the desired sensitivity. As stated, this included finding probe targets unique to *Mycoplasma pneumoniae*, and finding probe targets common to both *M. pneumoniae* and *M. genitalium*. This entailed finding sites which are:

(1) different between *M. pneumoniae* and *M. genitalium*, and (2) substantially the same within the two species' sequences, but different within the next closest evolutionary neighbors' sequences.

For this analysis, precise alignments of mycoplasma 16S and 23S rRNA sequences were developed. The essentially complete 16S rRNA and 23S rRNA sequences of both *M. pneumoniae* and *M. genitalium* were determined as part of this effort. Such nucleotide sequences were determined by standard laboratory protocols well known to those skilled in the art of probe design. The 16S and 23S rDNAs were cloned into plasmid vectors from products produced by enzymatic amplification. The *Mycoplasma pneumoniae* and *M. genitalium* sequences were aligned with homologous sequences of other mycoplasma and nonmycoplasma ribosomal RNA sequences. In addition to specifically addressing the close clinical and evolutionary relationship of *M. pneumoniae* to *M. genitalium*, the following additional 16S rRNA sequences were known and evaluated: *M. agalactiae*, *M. arginini*, *M. arthritidis*, *M. bovigenitalium*, *M. californicum*, *M. capricolum*, *M. ellychniae*, *M. melaleucum*, *M. fermentans*, *M. gallisepticum*, *M. hominis*, *M. hyopneumoniae*, *M. hyorhinis*, *M. iowae*, *M. lipophilum*, *M. mobile*, *M. muris*, *M. mycoides*, *M. neurolyticum*, *M. orale*, *M. pirum*, *M. pneumoniae*, *M. pulmonis*, *M. putrefaciens*, *M. salivarium*, *M. sualvi*, ten Spiroplasma species' sequences, four Acholeplasma species' sequences, four Anaeroplasma species' sequences, one Asteroleplasma sequence, and *Ureaplasma urealyticum* 16S rRNA sequence. (GenBank accession numbers shown in Weisburg et.al., Jnl. of Bacteriology, vol 171. 1989).

Twenty probes—designed, synthesized, and tested—are described by sequences in Tables 1 and 2. Nine probes specifically discriminate between *M. pneumoniae* and *M. genitalium*, eleven probes are uniquely inclusive for the pair of species. Probes which hybridize to both of the species have at least two benefits:

(1) as mentioned above, *M. genitalium* may be the cause of significant morbidity which is indistinguishable from that caused by *M. pneumoniae*, and (2) probes can be incorporated into dual probe assays in which only one of the probes requires the desired specificity.

Description of the Probes

The probe selection strategy yielded twenty probes useful for hybridization to the etiological agent of primary atypical pneumonia in samples.

Tables 1 and 2 describe the structure of the target regions and display the physical structure of the probes. Table 1 displays the precise alignment of the probe regions for both *Mycoplasma pneumoniae* and *Mycoplasma genitalium* along with the probe sequences designed from the aligned targets, Table 2 summarizes specific preferred nucleic acid compositions including length and G+C content.

The nucleic acid compositions of the invention should not be construed as restricted to the specific nucleotides identified with the named probes. Optimal probe length will be a function of the stringency of the hybridization conditions chosen. The sequences identified with the named probes are capable of some alteration and modification. Indeed, individuals skilled in the art will readily make adjustments in probe length and modified nucleotides to serve their specific assay and detection needs. For example, the length of these particular oligonucleotides was optimized for use in the dot blot assay and sandwich formats. In considering sets comprised of more than one probe, it is desirable that all probes behave in a compatible manner. Thus, the exact length of a particular probe will to a certain extent reflect its specific intended use.

The nucleic acid compositions of the present invention comprise sequences which can be employed as oligonucleotide probes, or could be incorporated into larger polynucleotides of either ribonucleic acid or deoxyribonucleic acid. Sequences complementary to the probes described herein can be used as probes to rRNA genes. The preferred probes or their complements can be employed as chain elongation initiators for polymerase chain reaction, sequencing or other applications.

EXAMPLES

EXAMPLE 1

Dot-Blot Analysis of Probe Hybridization Behavior

Dot-blot analysis, involves immobilizing a nucleic acid or a population of nucleic acids on a filter such as nitrocellulose, nylon, or other derivatized membranes which can readily be obtained commercially, specifically for this purpose. Either DNA or RNA can be easily immobilized on such a filter and subsequently can be probed or tested for hybridization under any of a variety of conditions i.e., stringencies) with nucleic acid compositions or probes of interest. Nucleic acids which have sequences with greater complementarity to a target will form hybridization reaction products which are more stable than probes containing less complementarity. Indeed, the added stability can be exploited to allow nucleic acids having sequences complementary to a target to bind preferentially to target without substantial hybridization to nontarget nucleic acids.

Probes of the present invention were tested in a dot-blot format. One hundred nanograms of RNA, purified by phenol extraction and centrifugation through cesium trifluoroacetate gradients, was denatured and spotted on a nylon membrane. Probes were isotopically labelled with the addition of a $^{32}$Phosphorous moiety to the 5' end of the oligonucleotide. Hybridization of probes occurred, at a temperature of 60° C. in the presence of 1.08M sodium chloride, 60 mM sodium phosphate, and 6 mM ethylenediamine tetraacetic acid, pH 7.4. Unhybridized probe was removed by washing at a salt concentration one-third of the hybridization condition. The filters were exposed to X-ray film and the intensity of hybridization signals was evaluated after three hours of exposure.

The experimental specificity of the preferred probes, as described in Example 1 is summarized in Tables 2 and 3. Table 3 displays the hybridization behavior of the probes for a panel of clinically and environmentally representative mycoplasma species.

The 10 representative strains of *Mycoplasma pneumoniae* and 3 strains of *M. genitalium* represent a selection from the National Institute of Allergy and Infectious Disease's Mycoplasma Section. Additional species of bacteria and a few fungi were added to the panel in order to represent the breadth of known bacterial taxa. *Mycoplasma gallisepticum* is critically important as a representative close relative of the *M. pneumoniae/M. genitalium* cluster.

All species on the panel are represented by 100 ng of purified, denatured RNA. Probes were synthesized (by standard methods and chemistries well known to those skilled in the art), $^{32}$Phosphorous labelled, hybridized to panels under standard conditions, at the temperatures indicated, and auto-radiographically evaluated. "++++" represents strongest hybridization signal after three hours exposure, with slightly lighter signal represented by "+++", diminishing to "++", then "+". "+−" is virtually absent, and "−" is indicative of no hybridization of probe to target. The specificity is empirical and in the case of several of the *M. pneumoniae+M. genitalium* probes represents a slight departure from the predicted specific behavior.

EXAMPLE 2

Dual Probe Hybridization

In actual practice, many applications of these probes would employ a pair of probes being used simultaneously in a "sandwich" hybridization scheme. Turning now to FIG. 1, a sandwich assay is depicted featuring a capture probe 12 and a detector probe 13. The capture probe 12 ideally would be a bifunctional nucleic acid manufactured by adding a homopolymeric 3' tail to a probe with high target specificity. The tail would, in turn, hybridize to the complementary homopolymer 11 on a solid surface 10, such as a glass bead or a filter disc. Hybridization of the capture probe 12 to its target 15, in this case mycoplasma rRNA, would complex the target 15 with the solid support 10. The detector probe 13, advantageously also with some degree of specificity, would be part of a detection scheme relying on radioactivity, fluorescence, chemiluminescence, color, and other detection means, detection moiety 14 which would report the presence of the entire hybridization complex. The detector probe could potentially be incorporated as an RNA sequence into an amplifiable Q-beta midivariant as described by Kramer and Lizardi (Nature, vol. 339, 1989).

EXAMPLE 3

Clinical Diagnosis of *Mycoplasma pneumoniae* Primary Atypical Pneumonia

A clinical sample, such as a swab, sputum, or tissue is processed so as to liberate the total nucleic acid content. The sample, containing disrupted mycoplasmas is incubated in the presence of capture probe, detector probe, and magnetic particle beads which have been derivatized with oligo-Thymidine—as in Example 2—in a chaotropic buffer such as guanidinium isothiocyanate.

If target molecules, *Mycoplasma pneumoniae* or *M. genitalium* 16S or 23S rRNA (depending on which probe sets are employed) are present, a Bead+Capture Probe+Target+Detector Probe hybridization complex is formed, as in FIG. 1. The presence of a magnet near the bottom of the reaction tube will cause the magnetic particle+hybridization complex to adhere to the side of the tube enabling removal of the sample matrix, unbound probe, etc. Repeated rehydration and denaturation of the bead+probe+target complex would enable significant background reduction (as described in U.S. Ser. No. 922,155, Collins, 1986, now abandoned). In this example, final detection could entail spotting the beads on membrane and assaying by autoradiography. Alternatively, the detector probe could be an amplifiable midivariant probe.

For this particular assay, the following capture and detector probes are examples of preferred pairs:

Probe 2196 (SEQ ID NO:9)+Probe 2167 (SEQ ID NO:8), Probe 2162 (SEQ ID NO:13)+Probe 2202 (SEQ ID NO:14)

Probe 2224 (SEQ ID NO:17)+ Probe 2166 (SEQ ID NO:16), Probe 2162 (SEQ ID NO:13)+Probe 2230 (SEQ ID NO:20)

Probe 2167 (SEQ ID NO:8)+Probe 2219 (SEQ ID NO:12), Probe 2192 (SEQ ID NO:11)+Probe 2202 (SEQ ID NO:14)

Probe 2296 (SEQ ID NO:3)+Probe 2297 (SEQ ID NO:10), Probe 2299 (SEQ ID NO:5)+Probe 2300 (SEQ ID NO:6)

EXAMPLE 4

Clinical Diagnosis of *M. pneumoniae* Primary Atypical Pneumonia from Human Sample Employing Polymerase Chain Reaction Amplification of Mycoplasma rDNA Sample processing is designed so as to yield DNA. One of the probes described herein is used in conjunction with the antiparallel complement of one of the probes described herein to enzymatically amplify a segment of *Mycoplasma pneumoniae* or *M. genitalium* gene encoding mycoplasma rRNA in a polymerase chain reaction. Resultant material can then be assayed in a "sandwich" hybridization assay with any of the probes described herein. The polymerase chain reaction can, itself, be made either highly specific by employing probe/primers described herein, or the reaction can be made more general using less specific probes, and identifying the amplification product as *M. pneumoniae* with probes described herein which have great specificity.

EXAMPLE 5

In Situ Hybridization as a Cytological Stain

The probes of the present invention can be employed as cytological staining reagents. For example, a sputum sample is applied to a microscope slide. After appropriate fixation and lysis, hybridization of probes is carried out in situ. In this example, *Mycoplasma pneumoniae* could be visualized in a specimen by fluorescently labelling Probe 2167 (SEQ ID NO:8) and examining the slide using a fluorescent microscope, looking for small fluorescent bodies.

EXAMPLE 6

Confirmation of *Mycoplasma pneumoniae* Following Culture

Following a standard cultivation step for *Mycoplasma pneumoniae* or *M. genitalium,* for example on H-agar plates or SP-6 broth colony or liquid culture is tested for the presence of *M. pneumoniae* by employing Probes 2167 (SEQ ID NO:8) and 2196.

TABLE 1

*Mycoplasma pneumoniae* 23S Probe Targets and Probes

| | |
|---|---|
| M. pneumoniae | 3'-AGUGGUGCAUAACGAAAUUAACUGAUAAAUAAGUAGUUA-5' (SEQ ID NO: 21) |
| M. genitalium | 3'-AGUGGUGCAUAGCGAAAUUAAUUGAUACUUAAGCCnnnn-5' (SEQ ID NO: 29) |
| Probe 2295 | 5'-TCACCACGTATTGCTTTAATTGACTATTTATTCATCAAT-3' (SEQ ID NO: 1) |
| M. pneumoniae | 3'-GUUGGGGAUAGAUUACUAUUCAAACCGGACA-5' (SEQ ID NO: 22) |
| M. genitalium | 3'-GUUGGGGAUAGGAGUCUAUCCAAACCGGACA-5' (SEQ ID NO: 30) |
| Probe 2289 | 5'-CAACCCCTATCTAATGATAAGTTTGGCCTGT-3' (SEQ ID NO: 2) |
| M. pneumoniae | 3'-AAGAUAGCAAAAGUUCAGGUGUAACGUUCGGGAUG-5' (SEQ ID NO: 23) |
| M. genitalium | 3'-AAGAUAGGAAAAUUGAAGGUAUUACGUUCGGGAUG-5' (SEQ ID NO: 31) |
| Probe 2296 | 5'-TTCTATCGTTTTCAAGTCCACATTGCAAGCCCTAC-3' (SEQ ID NO: 3) |
| M. pneumoniae | 3'-ACCAAUGUCGAUCUAAUUGGGAUCUUCGAAAAGA-5' (SEQ ID NO: 24) |
| M. genitalium | 3'-ACCAAUGUCAAUUUAAUCGGGAUCGUCGAAAAGA-5' (SEQ ID NO: 32) |
| Probe 2298 | 5'-TGGTTACAGCTAGATTAACCCTAGAAGCTTTTCT-3' (SEQ ID NO: 4) |
| M. pneumoniae | 3'-GGAUAAGAGAUGUACUAUUACAGGACUAGUUAUAA-5' (SEQ ID NO: 25) |
| M. genitalium | 3'-GGAUAAGAGAUGUACCACCACAAAACUAGUUAUAA-5' (SEQ ID NO: 33) |
| Probe 2299 | 5'-CCTATTCTCTACATGATAATGTCCTGATCAATATT-3' (SEQ ID NO: 5) |
| M. pneumoniae | 3'-AUCAUAAGGUGGAAAGCGUAGUUGUUCAGGAUCGCUUGA-5' (SEQ ID NO: 26) |
| M. genitalium | 3'-AUCAUAAGGUGUAAAGUGUAGUUGUUUAGGAACGCUUGA-5' (SEQ ID NO: 34) |
| Probe 2300 | 5'-TAGTATTCCACCTTTCGCATCAACAAGTCCTAGCGAACT-3' (SEQ ID NO: 6) |
| M. pneumoniae | 3'-AUCUUCGUUGUGAGAAGUUAGAAGGAUGCCCGUGUUA-5' (SEQ ID NO: 27) |
| M. genitalium | 3'-AUCUUCGUUUCGAGAAGUUAGAAGGACACCCGUGUUA-5' (SEQ ID NO: 35) |
| Probe 2294 | 5'-TAGAAGCAACACTCTTCAATCTTCCTACGGGCACAAT-3' (SEQ ID NO: 7) |

TABLE 1-continued

*Mycoplasma pneumoniae* 16S Probe Targets and Probes

| | |
|---|---|
| M. pneumoniae | 3'-GGUUAAACGUAAUCGUCAGAGCGAUCUGUUACAUUGA-5' (SEQ ID NO: 37) |
| M. genitalium | 3'-GGUUAAAUGUAAUCGUCAGAGCAAUUUGUUACAUUGA-5' (SEQ ID NO: 49) |
| Probe 2167 | 5'-CCAATTTGCATTAGCAGTCTCGCTAGACAATGTAACT-3' (SEQ ID NO: 8) |
| M. pneumoniae | 3'-GAAAUGUCUAAACGAGUGAAAAUGUUCGACCGCUGACA-5' (SEQ ID NO: 38) |
| M. genitalium | 3'-GAAAAGUCUAAACGAGUGAAAAUGUUCAACCGAUGACA-5' (SEQ ID NO: 50) |
| Probe 2196 | 5'-CTTTACAGATTTGCTCACTTTTACAAGCTGGCGACTGT-3' (SEQ ID NO: 9) |

*Mycoplasma pneumoniae* + *M. genitalium* 23S Probe Targets and Probes

| | |
|---|---|
| M. pneumoniae | 3'-CGAUAGUGGGAAAACGCGCGACGAAAGGUUG-5' (SEQ ID NO: 28) |
| M. genitalium | 3'-CGAUAGUGGGAGAAACCGCGACGAAAGGUUG-5' (SEQ ID NO: 36) |
| Probe 2297 | 5'-GCTATCACCCTTTTGCGCGCTGCTTTCCAAT-3' (SEQ ID NO: 10) |

*Mycoplasma pneumoniae* + *M. genitalium* 16S Probe Targets and Probes

| | |
|---|---|
| M. pneumoniae | 3'-GGGAGUAGUUUAUUGCUUGGGAACGUCCAGGA-5' (SEQ ID NO: 39) |
| M. genitalium | 3'-GGGAGUAGUUUAUUGCUUGGGAACGUCCAGGA-5' (SEQ ID NO: 51) |
| Probe 2192 | 5'-CCCTCATCAAATAACGAACCCTTGCAGGTCCT-3' (SEQ ID NO: 11) |
| M. pneumoniae | 3'-GGAGGUAAUACAAAGGUAUUGAAACGGUUCCUACA-5' (SEQ ID NO: 40) |
| M. genitalium | 3'-GGAGGUAAUACAAAGGUAUUGAAACGGUUCCUACA-5' (SEQ ID NO: 52) |
| Probe 2219 | 5'-CCTCCATTATGTTTCCATAACTTTGCCAAGGATGT-3' (SEQ ID NO: 12) |
| M. pneumoniae | 3'-GCGGAGAUUUCAUAAUGAUGAAAGCUAGCUGAACGUACA-5' (SEQ ID NO: 41) |
| M. genitalium | 3'-GCGGAGAUUUCAUAACGAUGAAGGCUAGCUGAACGUACA-5' (SEQ ID NO: 53) |
| Probe 2162 | 5'-CGCCTCTAAAGTATTACTACTTTCGATCGACTTGCATGT-3' (SEQ ID NO: 13) |
| M. pneumoniae | 3'-GAAACUAAGUACGCUUGGUUUCAAGAAUACGCCAUAAUCGAUCAGAAAG-5' (SEQ ID NO: 42) |
| M. genitalium | 3'-GAAAUUAAGUACGCUUGAUUUCAAGAAUACGCCAUAAUCGAUCAAAAAG-5' (SEQ ID NO: 54) |
| Probe 2202 | 5'-CTTTGATTCATGCGAACCAAAGTTCTTATGCGGTATTAGCTAGTCTTTC-3' (SEQ ID NO: 14) |
| M. pneumoniae | 3'-GUUUUACCAUGUCAGUUUGAGAUCGGUAAUGGACGAUUUCAGUAAG-5' (SEQ ID NO: 43) |
| M. genitalium | 3'-GUUUCACCAUGUCAGUUUGAGGUCGGUAACGGACGAUCUCAGUAAG-5' (SEQ ID NO: 55) |
| Probe 2201 | 5'-CAAAATGGTACAGTCAAACTCTAGCCATTACCTGCTAAAGTCATTC-3' (SEQ ID NO: 15) |
| M. pneumoniae | 3'-GAGGGAUGGUGUGAGAUCUAAUUAUCAAAGGUUACG-5' (SEQ ID NO: 44) |
| M. genitalium | 3'-GAGGGAUGGUGUGAGAUCUGACUAUCAAAGGUUACG-5' (SEQ ID NO: 56) |
| Probe 2166 | 5'-CTCCCTACCACACTCTAGATTAATAGTTTCCAATGC-3' (SEQ ID NO: 16) |
| M. pneumoniae | 3'-GUGAUGGCUCCCCUAGCGGGGCUGUCGAUCAUAGAUAGCA-5' (SEQ ID NO: 45) |
| M. genitalium | 3'-GUGAUGGCUUC-CUAGCGAGGCUGUCGAUCAUAGAUAGCA-5' (SEQ ID NO: 57) |
| Probe 2224 | 5'-CACTACCGAGGGGATCGCCCCGACAGCTAGTATCTATCGT-3' (SEQ ID NO: 17) |
| M. pneumoniae | 3'-CGAGUGAAAAUGUUCGACCGCUGACAAACAUAACCGG-5' (SEQ ID NO: 46) |
| M. genitalium | 3'-CGAGUGAAAAUGUUCAACCGAUGACAAACAUAACCGG-5' (SEQ ID NO: 58) |
| Probe 2195 | 5'-GCTCACTTTTACAAGCTGGCGACTGTTTGTATTGGCC-3' (SEQ ID NO: 18) |
| M. pneumoniae | 3'-GAAAUGUCUAAACGAGUGAAAAUGUUCGACCGCUGACA-5' (SEQ ID NO: 47) |
| M. genitalium | 3'-GAAAAGUCUAAACGAGUGAAAAUGUUCAACGAUGACA-5' (SEQ ID NO: 59) |
| Probe 2225 | 5'-CTTTTCAGATTTGCTCACTTTTACAAGTTGGCTACTGT-3' (SEQ ID NO: 19) |
| M. pneumoniae | 3'-GAAACUAAGUACGCUUGGUUUCAAGAAUACGCCAUAAUCGAUCAGAAAG-5' (SEQ ID NO: 48) |
| M. genitalium | 3'-GAAAUUAAGUACGCUUGAUUUCAAGAAUACGCCAUAAUCGAUCAAAAAG-5' (SEQ ID NO: 60) |
| Probe 2230 | 5'-CTTTAATTCATGCGAACTAAAGTTCTTATGCGGTATTAGCTAGTTTTTC-3' (SEQ ID NO: 20) |

TABLE 2

*Mycoplasma pneumoniae* 23S Probes

*Mycoplasma pneumoniae* Probe 2295 (SEQ ID NO: 1) (38mer 28% G + C)
5'-TCA CCA CGT ATT GCT TTA ATT GAC TAT TTA TTC ATC AAT-3'
*Mycoplasma pneumoniae* Probe 2289 (SEQ ID NO: 2) (31mer 42% G + C)
5'-CAA CCC CTA TCT AAT GAT AAG TTT GGC CTG T-3'
*Mycoplasma pneumoniae* Probe 2296 (SEQ ID NO: 3) (35mer 43% G + C)
5'-TTC TAT CGT TTT CAA GTC CAC ATT GCA AGC CCT AC-3'
*Mycoplasma pneumoniae* Probe 2298 (SEQ ID NO: 4) (34mer 38% G + C)
5'-TGG TTA CAG CTA GAT TAA CCC TAG AAG CTT TTC T-3'
*Mycoplasma pneumoniae* Probe 2299 (SEQ ID NO: 5) (35mer 31% G + C)
5'-CCT ATT CTC TAC ATG ATA ATG TCC TGA TCA ATA TT-3'
*Mycoplasma pneumoniae* Probe 2300 (SEQ ID NO: 6) (39mer 44% G + C)
5'-TAG TAT TCC ACC TTT CGC ATC AAC AAG TCC TAG CGA ACT-3'
*Mycoplasma pneumoniae* Probe 2294 (SEQ ID NO: 7) (37mer 43% G + C)
5'-TAG AAG CAA CAC TCT TCA ATC TTC CTA CGG GCA CAA T-3'

*Mycoplasma pneumoniae* 16S Probes

*Mycoplasma pneumoniae* Probe 2167 (SEQ ID NO: 8) (37mer 41% G + C)
5'-CCA ATT TGC ATT AGC AGT CTC GCT AGA CAA TGT AAC T-3'
*Mycoplasma pneumoniae* Probe 2196 (SEQ ID NO: 9) (38mer 42% G + C)
5'-CTT TAC AGA TTT GCT CAC TTT TAC AAG CTG GCG ACT GT-3'

*Mycoplasma pneumoniae* + *M. genitalium* 23S Probes

TABLE 2-continued

*M. pneumoniae + M. genitalium* Probe 2297 (SEQ ID NO: 10) (31mer 52% G + C)
5'-GCT ATC ACC CTT TTG CGC GCT GCT TTC CAA T-3'

Mycoplasma pneumoniae + M. genitalium 16S Probes

*M. pneumoniae + M. genitalium* Probe 2192 (SEQ ID NO: 11) (32mer 50% G + C)
5'-CCC TCA TCA AAT AAC GAA CCC TTG CAG GTC CT-3'
*M. pneumoniae + M. genitalium* Probe 2219 (SEQ ID NO: 12) (35mer 40% G + C)
5'-CCT CCA TTA TGT TTC CAT AAC TTT GCC AAG GAT GT-3'
*M. pneumoniae + M. genitalium* Probe 2162 (SEQ ID NO: 13) (39mer 41% G + C)
5'-CGC CTC TAA AGT ATT ACT ACT TTC GAT CGA CTT GCA TGT-3'
*M. pneumoniae + M. genitalium* Probe 2202 (SEQ ID NO: 14) (49mer 39% G + C)
5'-CTT TGA TTC ATG CGA ACC AAA GTT CTT ATG CGG TAT TAG CTA GTC TTT C-3'
*M. pneumoniae + M. genitalium* Probe 2201 (SEQ ID NO: 15) (46mer 39% G + C)
5'-CAA AAT GGT ACA GTC AAA CTC TAG CCA TTA CCT GCT AAA GTC ATT C-3'
*M. pneumoniae + M. genitalium* Probe 2166 (SEQ ID NO: 16) (36mer 42% G + C)
5'-CTC CCT ACC ACA CTC TAG ATT AAT AGT TTC CAA TGC-3'
*M. pneumoniae + M. genitalium* Probe 2224 (SEQ ID NO: 17) (40mer 57% G + C)
5'-CAC TAC CGA GGG GAT CGC CCC GAC AGC TAG TAT CTA TCG T-3'
*M. pneumoniae + M. genitalium* Probe 2195 (SEQ ID NO: 18) (37mer 49% G + C)
5'-GCT CAC TTT TAC AAG CTG GCG ACT GTT TGT ATT GGC C-3'
*M. pneumoniae + M. genitalium* Probe 2225 (SEQ ID NO: 19) (38mer 38% G + C)
5'-CTT TTC AGA TTT GCT CAC TTT TAC AAG TTG GCT ACT GT-3'
*M. pneumoniae + M. genitalium* Probe 2230 (SEQ ID NO: 20) (49mer 33% G + C)
5'-CTT TAA TTC ATG CGA ACT AAA GTT CTT ATG CGG TAT TAG CTA GTT TTT C-3'

TABLE 3

Mycoplasma pneumoniae specific probes Targeting the 16S rRNA

| Strain designation | Genus/species | PROBE 2167 (SEQ ID NO: 8) | 2196 (SEQ ID NO: 9) |
|---|---|---|---|
| FH-300 | Mycoplasma pneumoniae | ++++ | ++++ |
| PI1428 | Mycoplasma pneumoniae | ++++ | ++++ |
| TW10-5P | Mycoplasma pneumoniae | ++++ | ++++ |
| TW10-6P | Mycoplasma pneumoniae | ++++ | ++++ |
| TW48-5P | Mycoplasma pneumoniae | ++++ | +++ |
| R32-P | Mycoplasma pneumoniae | ++++ | +++ |
| TW8-6P | Mycoplasma pneumoniae | ++++ | +++ |
| TW25-40 | Mycoplasma pneumoniae | ++++ | +++ |
| TM14-4 | Mycoplasma pneumoniae | ++++ | +++ |
| TW11-4 | Mycoplasma pneumoniae | ++++ | ++++ |
| 33530 G-37 | Mycoplasma genitalium | +– | +– |
| TW10-5G | Mycoplasma genitalium | +– | +– |
| UTMB-10G | Mycoplasma genitalium | +– | +– |
| 25960 | Mycoplasma pirum | +– | +– |
| 19610 | Mycoplasma gallisepticum | +– | – |
| 23114 PG21 | Mycoplasma hominis PG21 | – | – |
| 15718 KS-1 | Mycoplasma putrefaciens | – | – |
| serotype 8 | Ureaplasma urealyticum | – | – |
| 23206 PG8 | Acholeplasma laidlawii | – | – |
| IG 3224 | Citrobacter freundii | – | – |
| IG 3157 | Escherichia coli | – | – |
| 33391 | Haemophilus influenzae | – | – |
| 13077 | Neisseria meningitidis A | – | – |
| 15955 | Agrobacterium tumefaciens | – | – |
| 7757 | Desulfovibrio desulfuricans | – | – |
| 33560 | Campylobacter jejuni | – | – |
| 13124 | Clostridium perfringens | – | – |
|  | Spirochaeta aurantia | – | – |
| 25285 | Bacteroides fragilis | – | – |
|  | Stool RNA | – | – |
|  | Wheat Germ | – | – |
|  | Human CaSKi | – | – |
| 18804 | Candida albicans | – | – |
| 32045 | Cryptococcus neoformans | – | – |

Mycoplasma pneumoniae specific probes Targeting the 23S rRNA

| Strain designation | Genus/species | 2295 (SEQ ID NO: 1) | 2289 (SEQ ID NO: 2) | 2296 (SEQ ID NO: 3) | 2298 (SEQ ID NO: 4) | 2299 (SEQ ID NO: 5) | 2300 (SEQ ID NO: 6) | 2294 (SEQ ID NO: 7) |
|---|---|---|---|---|---|---|---|---|

TABLE 3-continued

| Strain designation | Genus/species | | | | | | | |
|---|---|---|---|---|---|---|---|---|
| FH-300 | *Mycoplasma pneumoniae* | ++++ | +++ | ++++ | +++ | +++ | +++ | +++ |
| PI1428 | *Mycoplasma pneumoniae* | ++++ | +++ | +++ | +++ | +++ | +++ | +++ |
| TW10-5P | *Mycoplasma pneumoniae* | ++++ | ++++ | +++ | +++ | ++++ | +++ | +++ |
| TW10-6P | *Mycoplasma pneumoniae* | ++++ | ++++ | +++ | +++ | ++++ | +++ | ++ |
| TW48-5P | *Mycoplasma pneumoniae* | ++++ | ++++ | +++ | ++++ | ++++ | +++ | ++ |
| R32-P | *Mycoplasma pneumoniae* | ++++ | ++++ | ++++ | ++++ | ++++ | ++++ | ++++ |
| TW8-6P | *Mycoplasma pneumoniae* | +++ | ++++ | ++++ | ++++ | ++++ | ++++ | +++ |
| TW25-40 | *Mycoplasma pneumoniae* | +++ | +++ | ++++ | ++++ | ++++ | ++++ | +++ |
| TW14-4 | *Mycoplasma pneumoniae* | +++ | +++ | ++++ | ++++ | +++ | ++++ | +++ |
| TH11-4 | *Mycoplasma pneumoniae* | +++ | +++ | ++++ | ++++ | +++ | ++++ | ++++ |
| 33530 G-37 | *Mycoplasma genitalium* | − | − | − | − | − | − | − |
| TW10-5G | *Mycoplasma genitalium* | − | − | − | − | − | − | − |
| UTMB-10G | *Mycoplasma genitalium* | − | − | − | − | − | − | − |
| 25960 | *Mycoplasma pirum* | − | − | − | − | − | − | − |
| 19610 | *Mycoplasma gallisepticum* | − | − | − | − | − | − | − |
| 23114 PG21 | *Mycoplasma hominis* PG21 | − | − | − | − | − | − | − |
| 15718 KS-1 | *Mycoplasma putrefaciens* | − | − | − | − | − | − | − |
| PG18 | *Mycoplasma fermentans* | − | − | − | − | − | − | − |
| 33552 | *Mycoplasma iowae* | − | − | − | − | − | − | − |
| KD735 | *Mycoplasma pulmonis* | − | − | − | − | − | − | − |
| 23206 PG8 | *Acholeplasma laidlawii* | − | − | − | − | − | − | − |
| IG 3224 | *Citrobacter freundii* | − | − | − | − | − | − | − |
| IG 3157 | *Escherichia coli* | − | − | − | − | − | − | − |
| 33391 | *Haemophilus influenzae* | − | − | − | − | − | − | − |
| 13077 | *Neisseria meningitidis* A | − | − | − | − | − | − | − |
| 15955 | *Agrobacterium tumefaciens* | − | − | − | − | − | − | − |
| 7757 | *Desulfovibrio desulfuricans* | − | − | − | − | − | − | − |
| 33560 | *Campylobacter jejuni* | − | − | − | − | − | − | − |
| 13124 | *Clostridium perfringens* | − | − | − | − | − | − | − |
| | *Spirochaeta aurantia* | − | − | − | − | − | − | − |
| 25285 | *Bacteroides fragilis* | − | − | − | − | − | − | − |
| | Stool RNA | − | − | − | − | − | − | − |
| | Wheat Germ | − | − | − | − | − | − | − |
| | Human CaSKi | − | − | − | − | − | − | − |
| 18804 | *Candida albicans* | − | − | − | − | − | − | − |
| 32045 | *Cryptococcus neoformans* | − | − | − | − | − | − | − |

*Mycoplasma pneumoniae* + *Mycoplasma genitalium* specific probes Targeting the 16S rRNA

| Strain designation | Genus/species | PROBE | | | | |
|---|---|---|---|---|---|---|
| | | 2192 (SEQ ID NO: 11) | 2219 (SEQ ID NO: 12) | 2162 (SEQ ID NO: 13) | 2202 (SEQ ID NO: 14) | 2201 (SEQ ID NO: 15) |
| FH-300 | *Mycoplasma pneumoniae* | ++++ | ++++ | ++++ | ++++ | ++++ |
| PI1428 | *Mycoplasma pneumoniae* | ++++ | ++++ | +++ | ++++ | ++++ |
| TW10-5P | *Mycoplasma pneumoniae* | ++++ | ++++ | ++ | ++ | +++ |
| TW10-6P | *Mycoplasma pneumoniae* | +++ | ++++ | +++ | ++ | +++ |
| TW48-5P | *Mycoplasma pneumoniae* | +++ | ++++ | +++ | ++ | +++ |
| R32-P | *Mycoplasma pneumoniae* | +++ | ++++ | +++ | ++ | +++ |
| TW8-6P | *Mycoplasma pneumoniae* | +++ | ++++ | +++ | ++ | +++ |
| TW25-40 | *Mycoplasma pneumoniae* | ++++ | ++++ | ++ | ++ | +++ |
| TW14-4 | *Mycoplasma pneumoniae* | +++ | ++++ | ++ | ++ | +++ |
| TW11-4 | *Mycoplasma pneumoniae* | +++ | ++++ | ++ | ++ | +++ |
| 33530 G-37 | *Mycoplasma genitalium* | ++++ | ++++ | +++ | +++ | +++ |
| TW10-5G | *Mycoplasma genitalium* | ++++ | ++++ | ++++ | +++ | ++ |
| UTMB-10G | *Mycoplasma genitalium* | +++ | ++++ | +++ | ++ | ++ |
| 25960 | *Mycoplasma pirum* | − | − | ++ | − | − |
| 19610 | *Mycoplasma gallisepticum* | − | − | ++ | − | − |
| 23114 PG21 | *Mycoplasma hominis* PG21 | − | − | − | − | − |
| 15718 KS-1 | *Mycoplasma putrefaciens* | − | − | − | − | − |
| serotype 8 | *Ureaplasma urealyticum* | − | − | − | − | − |
| 23206 PG8 | *Acholeplasma laidlawii* | − | − | − | − | − |
| IG 3224 | *Citrobacter freundii* | − | − | − | − | − |
| IG 3157 | *Escherichia coli* | − | − | − | − | − |
| 33391 | *Haemophilus influenzae* | − | − | − | − | − |
| 13077 | *Neisseria meningitidis* A | − | − | − | − | − |
| 15955 | *Agrobacterium tumefaciens* | − | − | − | − | − |
| 7757 | *Desulfovibrio desulfuricans* | − | − | − | − | − |
| 33560 | *Campylobacter jejuni* | − | − | − | − | − |
| 13124 | *Clostridium perfringens* | − | − | − | − | − |
| | *Spirochaeta aurantia* | − | − | − | − | − |
| 25285 | *Bacteroides fragilis* | − | − | − | − | − |
| | Stool RNA | − | − | − | − | − |
| | Wheat Germ | − | − | − | − | − |
| | Human CaSKi | − | − | − | − | − |
| 18804 | *Candida albicans* | − | − | − | − | − |
| 32045 | *Cryptococcus neoformans* | − | − | − | − | − |

TABLE 3-continued

| | | | | | | |
|---|---|---|---|---|---|---|
| | Mycoplasma fermentans | – | – | – | – | – |
| | Mycoplasma iowae | – | – | – | – | – |
| | Mycoplasma pulmonis | – | – | – | – | – |

| | | PROBE | | | | |
|---|---|---|---|---|---|---|
| Strain designation | Genus/species | 2166 (SEQ ID NO: 16) | 2224 (SEQ ID NO: 17) | 2195 (SEQ ID NO: 18) | 2225 (SEQ ID NO: 19) | 2230 (SEQ ID NO: 20) |
| FH-300 | Mycoplasma pneumoniae | ++++ | +++ | ++++ | ++++ | ++++ |
| PI1428 | Mycoplasma pneumoniae | ++++ | ++++ | ++++ | ++++ | ++++ |
| TW10-5P | Mycoplasma pneumoniae | ++++ | ++++ | ++++ | ++++ | ++++ |
| TW10-6P | Mycoplasma pneumoniae | ++++ | ++++ | ++++ | ++++ | ++++ |
| TW48-5P | Mycoplasma pneumeniae | ++++ | ++++ | ++++ | ++++ | ++++ |
| R32-P | Mycoplasma pneumoniae | ++++ | +++ | ++++ | ++++ | ++++ |
| TW8-6P | Mycoplasma pneumoniae | ++++ | +++ | ++++ | ++++ | ++++ |
| TW25-40 | Mycoplasma pneumoniae | ++++ | +++ | ++++ | ++++ | ++++ |
| TW14-4 | Mycoplasma pneumoniae | ++++ | +++ | ++++ | ++++ | ++++ |
| TW11-4 | Mycoplasma pneumoniae | ++++ | +++ | ++++ | ++++ | ++++ |
| 33530 G-37 | Mycoplasma genitalium | ++++ | +++ | ++++ | ++++ | ++++ |
| TW10-5G | Mycoplasma genitalium | ++++ | +++ | ++++ | ++++ | ++++ |
| UTMB-10G | Mycoplasma genitalium | ++++ | +++ | ++++ | ++++ | ++++ |
| 25960 | Mycoplasma pirum | – | – | – | – | – |
| 19610 | Mycoplasma gallisepticum | – | – | – | – | – |
| 23114 PG21 | Mycoplasma hominis PG21 | – | – | – | – | – |
| 15718 KS-1 | Mycoplasma putrefaciens | – | – | – | – | – |
| serotype 8 | Ureaplasma urealyticum | – | – | – | – | – |
| 23206 PG8 | Acholeplasma laidlawii | – | – | – | – | – |
| IG 3224 | Citrobacter freundii | – | – | – | – | – |
| IG 3157 | Escherichia coli | – | – | – | – | – |
| 33391 | Haemophilus influenzae | – | – | – | – | – |
| 13077 | Neisseria meningitidis A | – | – | – | – | – |
| 15955 | Agrobacterium tumefaciens | – | – | – | – | – |
| 7757 | Desulfovibrio desulfuricans | – | – | – | – | – |
| 33560 | Campylobacter jejuni | – | – | – | – | – |
| 13124 | Clostridium perfringens | – | – | – | – | – |
| | Spirochaeta aurantia | – | – | – | – | – |
| 25285 | Bacteroides fragilis | – | – | – | – | – |
| | Stool RNA | – | – | – | – | – |
| | Wheat Germ | – | – | – | – | – |
| | Human CaSKi | – | – | – | – | – |
| 18804 | Candida albicans | – | – | – | – | – |
| 32045 | Cryptococcus neoformans | – | – | – | – | – |
| | Mycoplasma fermentans | – | – | – | – | – |
| | Mycoplasma iowae | – | – | – | – | – |
| | Mycoplasma pulmonis | – | – | – | – | – |

*Mycoplasma pneumoniae + Mycoplasma genitalium* specific probes Targeting the 23S rRNA

| Strain designation | Genus/species | PROBE 2297 (SEQ ID NO: 10) |
|---|---|---|
| FH-300 | Mycoplasma pneumoniae | +++ |
| PI1428 | Mycoplasma pneumoniae | +++ |
| TW10-5P | Mycoplasma pneumoniae | +++ |
| TW10-6P | Mycoplasma pneumoniae | +++ |
| TW48-5P | Mycoplasma pneumeniae | +++ |
| R32-P | Mycoplasma pneumoniae | ++++ |
| TW8-6P | Mycoplasma pneumoniae | ++++ |
| TW25-40 | Mycoplasma pneumoniae | ++++ |
| TW14-4 | Mycoplasma pneumoniae | ++++ |
| TW11-4 | Mycoplasma pneumoniae | ++++ |
| 33530 G-37 | Mycoplasma genitalium | +++ |
| TW10-5G | Mycoplasma genitalium | +++ |
| UTMB-10G | Mycoplasma genitalium | +++ |
| 25960 | Mycoplasma pirum | +– |
| 19610 | Mycoplasma gallisepticum | – |
| 23114 PG21 | Mycoplasma hominis PG21 | – |
| 15718 KS-1 | Mycoplasma putrefaciens | +– |
| PG18 | Mycoplasma fermentans | – |
| 33552 | Mycoplasma iowae | – |
| KD735 | Mycoplasma pulmonis | – |
| 23206 PG8 | Acholeplasma laidlawii | – |
| IG 3224 | Citrobacter freundii | – |
| IG 3157 | Escherichia coli | – |
| 33391 | Haemophilus influenzae | – |
| 13077 | Neisseria meningitidis A | – |
| 15955 | Agrobacterium tumefaciens | – |
| 7757 | Desulfovibrio desulfuricans | – |
| 33560 | Campylobacter jejuni | – |

TABLE 3-continued

| | | |
|---|---|---|
| 13124 | *Clostridium perfringens* | – |
| | *Spirochaeta aurantia* | – |
| 25285 | *Bacteroides fragilis* | – |
| | Stool RNA | – |
| | Wheat Germ | – |
| | Human CaSKi | – |
| 18804 | *Candida albicans* | – |
| 32045 | *Cryptococcus neoformans* | – |

We claim:

1. An isolated nucleic acid consisting of a nucleotide sequence fully complementary or identical to any one of probes 2295 (SEQ ID NO:1), 2289 (SEQ ID NO:2), 2296 (SEQ ID NO:3), 2298 (SEQ ID NO:4), 2299 (SEQ ID NO:5), 2300 (SEQ ID NO:6), and 2294 (SEQ ID NO:7), and wherein said nucleic acid hybridizes to the 23S ribosomal RNA (rRNA) or ribosomal DNA (rDNA) of *Mycoplasma pneumoniae* under normal hybridization conditions and does not hybridize to rRNA or rDNA of non-*Mycoplasma pneumoniae* bacteria and humans under identical hybridization conditions.

2. A nucleic acid of claim 1, wherein said nucleic acid is fully complementary or identical to any one of probes 2295 (SEQ ID NO:1), 2296 (SEQ ID NO:3), 2298 (SEQ ID NO:4), and 2299 (SEQ ID NO:5).

3. An isolated nucleic acid consisting of a nucleotide sequence fully complementary or identical to probe 2297 (SEQ ID NO:10), and wherein said nucleic acid hybridizes to the 23S ribosomal RNA (rRNA) or ribosomal DNA (rDNA) of *Mycoplasma pneumoniae* and *Mycoplasma genitalium* under normal hybridization conditions and does not hybridize to rRNA or rDNA of non-*Mycoplasma pneumoniae* and non-*Mycoplasma genitalium* bacteria and humans under identical hybridization conditions.

4. A set of nucleic acids comprising at least two nucleic acids of claim 1.

5. A set of nucleic acids of claim 4 comprising probes 2299 (SEQ ID NO:5) and 2300 (SEQ ID NO:6).

6. A method for detecting the presence of *Mycoplasma pneumoniae* in a sample comprising:
   a) contacting said sample with at least one nucleic acid of claim 1;
   b) imposing hybridization conditions on the sample and said nucleic acid to allow said nucleic acid to hybridize to the rRNA or rDNA of *Mycoplasma pneumoniae*, if present in the sample, to form nucleic acid complexes, under conditions which do not allow said nucleic acid to form stable hybridized nucleic acid complexes with non-Mycoplasma bacteria; and
   c) detecting said nucleic acid complexes as an indication of the presence of *Mycoplasma pneumoniae* in the sample.

7. An isolated nucleic acid consisting of a nucleotide sequence fully complementary or identical to any one of probes 2162 (SEQ ID NO:13), 2166 (SEQ ID NO:16), and 2167 (SEQ ID NO:8), which nucleic acid hybridizes to the 16S rRNA or rDNA of *Mycoplasma pneumoniae* or *Mycoplasma genitalium* under normal hybridization conditions and does not hybridize to the ribosomal RNA (rRNA) or ribosomal DNA (rDNA) of non-*Mycoplasma pneumoniae* and non-*Mycoplasma genitalium* bacteria and humans under identical hybridization conditions.

8. A nucleic acid of claim 7, wherein said nucleic acid is fully complementary or identical to any one of probes 2166 (SEQ ID NO:16), and 2167 (SEQ ID NO:8).

9. A nucleic acid that is fully complementary or identical to any one of probes 2219 (SEQ ID NO:12), 2202 (SEQ ID NO:14), 2225 (SEQ ID NO:19), and 2230 (SEQ ID NO:20).

10. A set of nucleic acids comprising at least two nucleic acids, each nucleic acid having a different nucleotide sequence composition, and wherein a first nucleic acid is a nucleic acid of claim 7, and a second nucleic acid consists of a nucleotide sequence fully complementary or identical to any one of probes 2196 (SEQ ID NO:9), 2192 (SEQ ID NO:11), 2219 (SEQ ID NO:12), 2202 (SEQ ID NO:14), 2201 (SEQ ID NO:15), 2224 (SEQ ID NO:17), 2195 (SEQ ID NO:18), 2225 (SEQ ID NO:19), and 2230 (SEQ ID NO:20), and wherein said second nucleic acid hybridizes to the 16S rRNA or rDNA of *Mycoplasma pneumoniae* or *Mycoplasma genitalium* under normal hybridization conditions and does not hybridize to the rRNA or rDNA of non-*Mycoplasma pneumoniae* and non-*Mycoplasma genitalium* bacteria and humans under identical hybridization conditions.

11. A set of nucleic acids of claim 10 selected from the group of sets:
   2196 (SEQ ID NO:9) and 2167 (SEQ ID NO:8),
   2162 (SEQ ID NO:13) and 2202 (SEQ ID NO:14),
   2224 (SEQ ID NO:17) and 2166 (SEQ ID NO:16),
   2162 (SEQ ID NO:13) and 2230 (SEQ ID NO:20), and
   2167 (SEQ ID NO:8) and 2219 (SEQ ID NO:12).

12. A method for detecting the presence of *Mycoplasma pneumoniae* in a sample comprising:
   a) contacting said sample with at least one nucleic acid of claim 7;
   b) imposing hybridization conditions on the sample and said nucleic acid to allow said nucleic acid to hybridize to the rRNA or rDNA of *Mycoplasma pneumoniae*, if present in the sample, to form nucleic acid complexes, under conditions which do not allow said nucleic acid to form stable hybridized nucleic acid complexes with non-Mycoplasma bacteria; and
   c) detecting said nucleic acid complexes as an indication of the presence of *Mycoplasma pneumoniae* in the sample.

13. A method for detecting the presence of either one or both of *Mycoplasma pneumoniae* and *Mycoplasma genitalium* in a sample comprising:
   a) contacting said sample with a set of at least two nucleic acids of claim 10;
   b) imposing hybridization conditions on the sample and said nucleic acids to allow said nucleic acids to hybridize stably to the rRNA or rDNA of either one or both of *Mycoplasma pneumoniae* and *Mycoplasma genitalium*, if present in the sample, to form nucleic acid complexes, under conditions which do not allow said probe to form stable hybridized nucleic acid complexes with non-Mycoplasma bacteria; and
   c) detecting said nucleic acid complexes as an indication of the presence of either one or both of *Mycoplasma pneumoniae* and *Mycoplasma genitalium* in the sample.

14. A method of claim 13, wherein said set of nucleic acids is selected from the group of sets
   2196 (SEQ ID NO:9) and 2167 (SEQ ID NO:8),
   2162 (SEQ ID NO:13) and 2202 (SEQ ID NO:14),
   2224 (SEQ ID NO:17) and 2166 (SEQ ID NO:16),
   2162 (SEQ ID NO:13) and 2230 (SEQ ID NO:20), or
   2167 (SEQ ID NO:8) and 2219 (SEQ ID NO:12).

15. A probe consisting of a nucleic acid of claim 1 carrying one or more of an end cap, a detection moiety, an amplifiable Q-beta midivariant and a homopolymer nucleotide sequence.

16. A probe consisting of a nucleic acid of claim 3 carrying one or more of an end cap, a detection moiety, an amplifiable Q-beta midivariant and a homopolymer nucleotide sequence.

17. A probe consisting of a nucleic acid of claim 7 carrying one or more of an end cap, a detection moiety, an amplifiable Q-beta midivariant and a homopolymer nucleotide sequence.

18. A probe consisting of a nucleic acid of claim 9 carrying one or more of an end cap, a detection moiety, an amplifiable Q-beta midivariant and a homopolymer nucleotide sequence.

19. A probe consisting of a nucleic acid of claim 1 carrying an amplifiable Q-beta midivariant.

20. A probe consisting of a nucleic acid of claim 3 carrying an amplifiable Q-beta midivariant.

21. A probe consisting of a nucleic acid of claim 7 carrying an amplifiable Q-beta midivariant.

22. A probe consisting of a nucleic acid of claim 9 carrying an amplifiable Q-beta midivariant.

* * * * *

SEQUENCE LISTING ( 1 ) GENERAL INFORMATION:

( i i i ) NUMBER OF SEQUENCES: 60

( 2 ) INFORMATION FOR SEQ ID NO: 1:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 1:

TCACCACGTA TTGCTTTAAT TGACTATTTA TTCATCAAT        39

( 2 ) INFORMATION FOR SEQ ID NO: 2:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( x i ) SEQUENCE DESCRIPTION: SEQ ID NO: 2:

CAACCCCTAT CTAATGATAA GTTTGGCCTG T        31

( 2 ) INFORMATION FOR SEQ ID NO: 3:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 3:

TTCTATCGTT TTCAAGTCCA CATTGCAAGC CCTAC        35

( 2 ) INFORMATION FOR SEQ ID NO: 4:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( x i ) SEQUENCE DESCRIPTION: SEQ ID NO: 4:

TGGTTACAGC TAGATTAACC CTAGAAGCTT TTCT        34

( 2 ) INFORMATION FOR SEQ ID NO: 5:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 5:

CCTATTCTCT ACATGATAAT GTCCTGATCA ATATT 35

( 2 ) INFORMATION FOR SEQ ID NO: 6:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 6:

TAGTATTCCA CCTTTCGCAT CAACAAGTCC TAGCGAACT 39

( 2 ) INFORMATION FOR SEQ ID NO: 7:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 7:

TAGAAGCAAC ACTCTTCAAT CTTCCTACGG GCACAAT 37

( 2 ) INFORMATION FOR SEQ ID NO: 8:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 8:

CCAATTTGCA TTAGCAGTCT CGCTAGACAA TGTAACT 37

( 2 ) INFORMATION FOR SEQ ID NO: 9:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( x i ) SEQUENCE DESCRIPTION: SEQ ID NO: 9:

CTTTACAGAT TTGCTCACTT TTACAAGCTG GCGACTGT 38

( 2 ) INFORMATION FOR SEQ ID NO: 10:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( x i ) SEQUENCE DESCRIPTION: SEQ ID NO: 10:

GCTATCACCC TTTTGCGCGC TGCTTTCCAA T 31

( 2 ) INFORMATION FOR SEQ ID NO: 11:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 11:

CCCTCATCAA ATAACGAACC CTTGCAGGTC CT                     32

(2) INFORMATION FOR SEQ ID NO: 12:

(i) SEQUENCE CHARACTERISTICS:
        (A) LENGTH: 35
        (B) TYPE: nucleic acid
        (C) STRANDEDNESS: single
        (D) TOPOLOGY: linear (xi) SEQUENCE DESCRIPTION: SEQ ID NO: 12:

CCTCCATTAT GTTTCCATAA CTTTGCCAAG GATGT                  35

(2) INFORMATION FOR SEQ ID NO: 13:

(i) SEQUENCE CHARACTERISTICS:
        (A) LENGTH: 39
        (B) TYPE: nucleic acid
        (C) STRANDEDNESS: single
        (D) TOPOLOGY: linear (xi) SEQUENCE DESCRIPTION: SEQ ID NO: 13:

CGCCTCTAAA GTATTACTAC TTTCGATCGA CTTGCATGT              39

(2) INFORMATION FOR SEQ ID NO: 14:

(i) SEQUENCE CHARACTERISTICS:
        (A) LENGTH: 49
        (B) TYPE: nucleic acid
        (C) STRANDEDNESS: single
        (D) TOPOLOGY: linear (xi) SEQUENCE DESCRIPTION: SEQ ID NO: 14:

CTTTGATTCA TGCGAACCAA AGTTCTTATG CGGTATTAGC TAGTCTTTC   49

(2) INFORMATION FOR SEQ ID NO: 15:

(i) SEQUENCE CHARACTERISTICS:
        (A) LENGTH: 46
        (B) TYPE: nucleic acid
        (C) STRANDEDNESS: single
        (D) TOPOLOGY: linear (xi) SEQUENCE DESCRIPTION: SEQ ID NO: 15:

CAAAATGGTA CAGTCAAACT CTAGCCATTA CCTGCTAAAG TCATTC      46

(2) INFORMATION FOR SEQ ID NO: 16:

(i) SEQUENCE CHARACTERISTICS:
        (A) LENGTH: 36
        (B) TYPE: nucleic acid
        (C) STRANDEDNESS: single
        (D) TOPOLOGY: linear (xi) SEQUENCE DESCRIPTION: SEQ ID NO: 16:

CTCCCTACCA CACTCTAGAT TAATAGTTTC CAATGC                 36

(2) INFORMATION FOR SEQ ID NO: 17:

(i) SEQUENCE CHARACTERISTICS:
        (A) LENGTH: 40
        (B) TYPE: nucleic acid
        (C) STRANDEDNESS: single
        (D) TOPOLOGY: linear (xi) SEQUENCE DESCRIPTION: SEQ ID NO: 17:

CACTACCGAG GGGATCGCCC CGACAGCTAG TATCTATCGT             40

( 2 ) INFORMATION FOR SEQ ID NO: 18:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 18:

GCTCACTTTT ACAAGCTGGC GACTGTTTGT ATTGGCC                                    37

( 2 ) INFORMATION FOR SEQ ID NO: 19:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( x i ) SEQUENCE DESCRIPTION: SEQ ID NO: 19:

CTTTTCAGAT TTGCTCACTT TTACAAGTTG GCTACTGT                                   38

( 2 ) INFORMATION FOR SEQ ID NO: 20:

( i ) SEQUENCE CHARACTERISTICS:
        ( A ) LENGTH: 49
        ( B ) TYPE: nucleic acid
        ( C ) STRANDEDNESS: single
        ( D ) TOPOLOGY: linear ( x i ) SEQUENCE DESCRIPTION: SEQ ID NO: 20:

CTTTAATTCA TGCGAACTAA AGTTCTTATG CGGTATTAGC TAGTTTTTC                    49

( 2 ) INFORMATION FOR SEQ ID NO: 21:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 21:

AUUGAUGAAU AAAUAGUCAA UUAAAGCAAU ACGUGGUGA                                  39

( 2 ) INFORMATION FOR SEQ ID NO: 22:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( x i ) SEQUENCE DESCRIPTION: SEQ ID NO: 22:

ACAGGCCAAA CUUAUCAUUA GAUAGGGGUU G                                            31

( 2 ) INFORMATION FOR SEQ ID NO: 23:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 23:

GUAGGGCUUG CAAUGUGGAC UUGAAAACGA UAGAA                                      35

( 2 ) INFORMATION FOR SEQ ID NO: 24:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( x i ) SEQUENCE DESCRIPTION: SEQ ID NO: 24:

AGAAAAGCUU CUAGGGUUAA UCUAGCUGUA ACCA    34

( 2 ) INFORMATION FOR SEQ ID NO: 25:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 25:

AAUAUUGAUC AGGACAUUAU CAUGUAGAGA AUAGG    35

( 2 ) INFORMATION FOR SEQ ID NO: 26:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 26:

AGUUCGCUAG GACUUGUUGA UGCGAAAGGU GGAAUACUA    39

( 2 ) INFORMATION FOR SEQ ID NO: 27:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 27:

AUUGUGCCCG UAGGAAGAUU GAAGAGUGUU GCUUCUA    37

( 2 ) INFORMATION FOR SEQ ID NO: 28:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( x i ) SEQUENCE DESCRIPTION: SEQ ID NO: 28:

GUUGGAAAGC AGCGCGCAAA AGGGUGAUAG C    31

( 2 ) INFORMATION FOR SEQ ID NO: 29:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 29:

nnnnCCGAAU UCAUAGUUAA UUAAAGCGAU ACGUGGUGA    39

( 2 ) INFORMATION FOR SEQ ID NO: 30:

( i ) SEQUENCE CHARACTERISTICS:
    ( A ) LENGTH: 31
    ( B ) TYPE: nucleic acid
    ( C ) STRANDEDNESS: single
    ( D ) TOPOLOGY: linear ( x i ) SEQUENCE DESCRIPTION: SEQ ID NO: 30:

ACAGGCCAAA CCUAUCUGAG GAUAGGGGUU G          31

( 2 ) INFORMATION FOR SEQ ID NO: 31:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 31:

GUAGGGCUUG CAUUAUGGAA GUUAAAAGGA UAGAA          35

( 2 ) INFORMATION FOR SEQ ID NO: 32:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( x i ) SEQUENCE DESCRIPTION: SEQ ID NO: 32:

AGAAAAGCUG CAUGGGCUAA UUUAACUGUA ACCA          34

( 2 ) INFORMATION FOR SEQ ID NO: 33:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 33:

AAUAUUGAUC AAAACACCAC CAUGUAGAGA AUAGG          35

( 2 ) INFORMATION FOR SEQ ID NO: 34:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 34:

AGUUCGCAAG GAUUUGUUGA UGUGAAAUGU GGAAUACUA          39

( 2 ) INFORMATION FOR SEQ ID NO: 35:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 35:

AUUGUGCCCA CAGGAAGAUU GAAGAGCUUU GCUUCUA          37

( 2 ) INFORMATION FOR SEQ ID NO: 36:

( i ) SEQUENCE CHARACTERISTICS:
        ( A ) LENGTH: 31

(B) TYPE: nucleic acid
            (C) STRANDEDNESS: single
            (D) TOPOLOGY: linear (xi) SEQUENCE DESCRIPTION: SEQ ID NO: 36:

GUUGGAAAGC AGCGCCAAAG AGGGUGAUAG C                          31

(2) INFORMATION FOR SEQ ID NO: 37:

(i) SEQUENCE CHARACTERISTICS:
            (A) LENGTH: 37
            (B) TYPE: nucleic acid
            (C) STRANDEDNESS: single
            (D) TOPOLOGY: linear (xi) SEQUENCE DESCRIPTION: SEQ ID NO: 37:

AGUUACAUUG UCUAGCGAGA CUGCUAAUGC AAAUUGG                    37

(2) INFORMATION FOR SEQ ID NO: 38:

(i) SEQUENCE CHARACTERISTICS:
            (A) LENGTH: 38
            (B) TYPE: nucleic acid
            (C) STRANDEDNESS: single
            (D) TOPOLOGY: linear (xi) SEQUENCE DESCRIPTION: SEQ ID NO: 38:

ACAGUCGCCA GCUUGUAAAA GUGAGCAAAU CUGUAAAG                   38

(2) INFORMATION FOR SEQ ID NO: 39:

(i) SEQUENCE CHARACTERISTICS:
            (A) LENGTH: 32
            (B) TYPE: nucleic acid
            (C) STRANDEDNESS: single
            (D) TOPOLOGY: linear (xi) SEQUENCE DESCRIPTION: SEQ ID NO: 39:

AGGACCUGCA AGGGUUCGUU AUUUGAUGAG GG                         32

(2) INFORMATION FOR SEQ ID NO: 40:

(i) SEQUENCE CHARACTERISTICS:
            (A) LENGTH: 35
            (B) TYPE: nucleic acid
            (C) STRANDEDNESS: single
            (D) TOPOLOGY: linear (xi) SEQUENCE DESCRIPTION: SEQ ID NO: 40:

ACAUCCUUGG CAAAGUUAUG GAAACAUAAU GGAGG                      35

(2) INFORMATION FOR SEQ ID NO: 41:

(i) SEQUENCE CHARACTERISTICS:
            (A) LENGTH: 39
            (B) TYPE: nucleic acid
            (C) STRANDEDNESS: single
            (D) TOPOLOGY: linear (xi) SEQUENCE DESCRIPTION: SEQ ID NO: 41:

ACAUGCAAGU CGAUCGAAAG UAGUAAUACU UUAGAGGCG                  39

(2) INFORMATION FOR SEQ ID NO: 42:

(i) SEQUENCE CHARACTERISTICS:
            (A) LENGTH: 49
            (B) TYPE: nucleic acid
            (C) STRANDEDNESS: single ( D ) TOPOLOGY: linear ( x i ) SEQUENCE DESCRIPTION: SEQ ID NO: 42:

GAAAGACUAG CUAAUACCGC AUAAGAACUU UGGUUCGCAU GAAUCAAAG 49

( 2 ) INFORMATION FOR SEQ ID NO: 43:

( i ) SEQUENCE CHARACTERISTICS:
        ( A ) LENGTH: 46
        ( B ) TYPE: nucleic acid
        ( C ) STRANDEDNESS: single
        ( D ) TOPOLOGY: linear ( x i ) SEQUENCE DESCRIPTION: SEQ ID NO: 43:

GAAUGACUUU AGCAGGUAAU GGCUAGAGUU UGACUGUACC AUUUUG 46

( 2 ) INFORMATION FOR SEQ ID NO: 44:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 44:

GCAUUGGAAA CUAUUAAUCU AGAGUGUGGU AGGGAG 36

( 2 ) INFORMATION FOR SEQ ID NO: 45:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( x i ) SEQUENCE DESCRIPTION: SEQ ID NO: 45:

ACGAUAGAUA CUAGCUGUCG GGGCGAUCCC CUCGGUAGUG 40

( 2 ) INFORMATION FOR SEQ ID NO: 46:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 46:

GGCCAAUACA AACAGUCGCC AGCUUGUAAA AGUGAGC 37

( 2 ) INFORMATION FOR SEQ ID NO: 47:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( x i ) SEQUENCE DESCRIPTION: SEQ ID NO: 47:

ACAGUCGCCA GCUUGUAAAA GUGAGCAAAU CUGUAAAG 38

( 2 ) INFORMATION FOR SEQ ID NO: 48:

( i ) SEQUENCE CHARACTERISTICS:
        ( A ) LENGTH: 49
        ( B ) TYPE: nucleic acid
        ( C ) STRANDEDNESS: single
        ( D ) TOPOLOGY: linear ( x i ) SEQUENCE DESCRIPTION: SEQ ID NO: 48:

GAAAGACUAG CUAAUACCGC AUAAGAACUU UGGUUCGCAU GAAUCAAAG         49

( 2 ) INFORMATION FOR SEQ ID NO: 49:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 49:

AGUUACAUUG UUUAACGAGA CUGCUAAUGU AAAUGG                       37

( 2 ) INFORMATION FOR SEQ ID NO: 50:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( x i ) SEQUENCE DESCRIPTION: SEQ ID NO: 50:

ACAGUAGCCA ACUUGUAAAA GUGAGCAAAU CUGAAAAG                     38

( 2 ) INFORMATION FOR SEQ ID NO: 51:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 51:

AGGACCUGCA AGGGUUCGUU AUUUGAUGAG GG                           32

( 2 ) INFORMATION FOR SEQ ID NO: 52:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 52:

ACAUCCUUGG CAAAGUUAUG GAAACAUAAU GGAGG                        35

( 2 ) INFORMATION FOR SEQ ID NO: 53:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 53:

ACAUGCAAGU CGAUCGGAAG UAGCAAUACU UUAGAGGCG                    39

( 2 ) INFORMATION FOR SEQ ID NO: 54:

( i ) SEQUENCE CHARACTERISTICS:
        ( A ) LENGTH: 49
        ( B ) TYPE: nucleic acid
        ( C ) STRANDEDNESS: single
        ( D ) TOPOLOGY: linear ( x i ) SEQUENCE DESCRIPTION: SEQ ID NO: 54:

GAAAAACUAG CUAAUACCGC AUAAGAACUU UAGUUCGCAU GAAUUAAAG     49

( 2 ) INFORMATION FOR SEQ ID NO: 55:

( i ) SEQUENCE CHARACTERISTICS:
        ( A ) LENGTH: 46
        ( B ) TYPE: nucleic acid
        ( C ) STRANDEDNESS: single
        ( D ) TOPOLOGY: linear ( x i ) SEQUENCE DESCRIPTION: SEQ ID NO: 55:

GAAUGACUCU AGCAGGCAAU GGCUGGAGUU UGACUGUACC ACUUUG     46

( 2 ) INFORMATION FOR SEQ ID NO: 56:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 56:

GCAUUGGAAA CUAUCAGUCU AGAGUGUGGU AGGGAG     36

( 2 ) INFORMATION FOR SEQ ID NO: 57:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( x i ) SEQUENCE DESCRIPTION: SEQ ID NO: 57:

ACGAUAGAUA CUAGCUGUCG GAGCGAUCCU UCGGUAGUG     39

( 2 ) INFORMATION FOR SEQ ID NO: 58:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( x i ) SEQUENCE DESCRIPTION: SEQ ID NO: 58:

GGCCAAUACA AACAGUAGCC AACUUGUAAA AGUGAGC     37

( 2 ) INFORMATION FOR SEQ ID NO: 59:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( x i ) SEQUENCE DESCRIPTION: SEQ ID NO: 59:

ACAGUAGCCA ACUUGUAAAA GUGAGCAAAU CUGAAAAG     38

( 2 ) INFORMATION FOR SEQ ID NO: 60:

( i ) SEQUENCE CHARACTERISTICS:
        ( A ) LENGTH: 49
        ( B ) TYPE: nucleic acid
        ( C ) STRANDEDNESS: single
        ( D ) TOPOLOGY: linear ( x i ) SEQUENCE DESCRIPTION: SEQ ID NO: 60:

GAAAAACUAG CUAAUACCGC AUAAGAACUU UAGUUCGCAU GAAUUAAAG     49